United States Patent [19]

Pendleton

[11] Patent Number: 4,673,680

[45] Date of Patent: Jun. 16, 1987

[54] α$_2$-ADRENERGIC RECEPTOR ANTAGONISTS AS MODIFIERS OF GASTROINTESTINAL MOTILITY

[76] Inventor: Robert G. Pendleton, 980 Hertford Dr., Hatfield, Pa. 19440

[21] Appl. No.: 777,472

[22] Filed: Sep. 18, 1985

[51] Int. Cl.$^4$ .................... A61K 31/44; A61K 31/55; A61K 31/505

[52] U.S. Cl. .................................. 514/285; 514/212; 514/222; 514/226; 514/228; 514/231; 514/234; 514/235; 514/253; 514/256; 514/280; 514/275

[58] Field of Search ............... 514/285, 212, 222, 226, 514/228, 231, 234, 235, 253, 275, 256, 280

[56] References Cited

U.S. PATENT DOCUMENTS 3,132,147  5/1964  Schopf et al. ...................... 260/288

FOREIGN PATENT DOCUMENTS 1435573   5/1974  United Kingdom .
2083029A  3/1982  United Kingdom .
2106909   9/1982  United Kingdom .

OTHER PUBLICATIONS

Opalko et al., Indoquinolizines Chem. Abst. 96:162676j.
Kluze et al., Chem. Abstr. 91:204200d.

Primary Examiner—Frederick E. Waddell
Attorney, Agent, or Firm—William H. Nicholson; Michael C. Sudol

[57] ABSTRACT

Selective α$_2$-adrenergic receptor antagonists are effective in modifying gastrointestinal motility in a manner useful in the treatment of colonic spasm, irritable bowel syndrome and constipation.

5 Claims, No Drawings

$\alpha_2$-ADRENERGIC RECEPTOR ANTAGONISTS AS MODIFIERS OF GASTROINTESTINAL MOTILITY

RELATED APPLICATIONS

U.S. Ser. No. 755,863, filed July 17, 1985, discloses and claims some of the compounds useful in the novel method of treatment of this invention.

BACKGROUND OF THE INVENTION

This invention is concerned with selective $\alpha_2$-adrenoceptor antagonists which are of value as modifiers of gastro-intestinal motility in the treatment of colonic spasm, irritable bowel syndrome and constipation.

$\alpha_2$-Adrenergic receptor antagonism is generally associated with antidepressant, antidiabetic, antihypertensive, antiobesity and platelet aggregation inhibition activity. These compounds have now been found to modify gastrointestinal motility and are useful in the treatment of colonic spasm, irritable bowel syndrome and constipation.

DETAILED DESCRIPTION OF THE INVENTION

This invention is concerned with a novel method of treatment of colonic spasm, irritable bowel syndrome and constipation by the administration of a selective $\alpha_2$-adrenergic receptor antagonist to a patient in need of such treatment.

Known $\alpha_2$-adrenergic antagonists useful in the novel method of treatment of this invention are:

2-[2-(1,4-benzodioxanyl)]-2-imidazoline hydrochloride;
2-[2-phenyl-2-(2-pyridyl)ethyl]imidazoline dihydrochloride;
(RS,RS)-2-[$\alpha$-(2'-ethoxyphenoxy)benzyl]morpholine;
7,8-dichloro-1,2,3,4-tetrahydroisoquinoline;
1,3,4-14b-tetrahydro-2-methyl-10H-pyrazino[1,2-a]pyrrolo[2,1-c][1,4]benzodiazepine maleate;
2-(1-ethyl-2-imidazolyl)methyl-1,4-benzodioxane HCl;
2-(imidazoline-2-ylamino)isoindoline;
4-chloro-N-(4,5-dihydro-1H-imidazol-2-yl)-1,3-dihydro-2H-isoindol-2-amine monohydrochloride;
6-chloro-2,3,4,5-tetrahydro-3-methyl-1H-3-benzazepine;
2-[(o-cyclopropylphenoxy)methyl]-2-imidazoline;
2-amino-6(p-chlorobenzyl)4H-5,6,7,8-tetrahydrothiazolo [5,4-d]azepine dihydrochloride;
2-ethyl-2,3-dihydro-1,4-benzodioxin-2-yl)-2-imidazoline;
2-methyl-2,3-dihydro-1,4-benzodioxin-2-yl)-2-imidazoline;
2-n-propyl-2,3-dihydro-1,4-benzodioxin-2-yl)-2-imidazoline;
[2-(propen-2-yl)]-dihydro-1,4-benzodioxin-2-yl)-2-imidazoline;
DL-(imidazolinyl-2)-2-benzocyclobutane;
(+)-2-(2-imidazolinyl)-2,3-dihydrobenzofuranfumarate;
9-allyloxy-6-chloro-3-methyl-2,3-4,5-tetrahydro-1H-3-benzazepine;
2-amino-4-chloroindane;
[1,2,3]-thiadizolo[5,4-h]-6,7,8,9-tetrahydroisoquinoline;
N-methyl-N-(1,3,4,6,7,11ba-hexahydro-2H-benzo(a)-quinolizin-2B-yl)-isobutanesulfonamide;
N-methyl-N-(1,3,4,6,7,11b$\alpha$-hexahydro-2H-benzo[a]-quinolizin-2$\beta$-yl)-propanesulfonamide;
2-[(3,4-dihydro-2-naphthyl)methyl]-2-imidazoline;
2-(2,3-dihydro-1,4-benzodioxin-2-yl)-2-methoxyimidazoline hydrochloride;
1-[1-([indol-3-yl]methyl)piperid-4-yl]-3-benzoylurea;
2-(2,3-dihydro-1H-2-indenyl)-4,5-dihydro-1H-imidazole;
1,3,3a,9a-tetrahydro-2H-[1,4]benzodioxino[2,3-c]pyrrole;
2-methyl-1,3,3a,9a-tetrahydro-2H-[1,4]benzodioxino[2,3-c]pyrrole;
N-(2,11b)-1,3,4,6,7,11b-hexahydro-2H-benzo[a]quinolizin-2-yl]-N-(2-methanesulfonamidoethyl)methanesulfonamide;
N-(2,11b)-1,3,4,6,7,11b-hexahydro-2H-benzo[a]quinolizin-2-yl]-N-(2-methanesulfonamidoethyl)propanesulfonamide;
N-(2,11b)-1,3,4,6,7,11b-hexahydro-2H-benzo[a]quinolizin-2-yl]-N-(2-methanesulfonamidoethyl)benzenesulfonamide.

In addition to the foregoing and of particular interest in the novel method of this invention is the compound of structural formula:

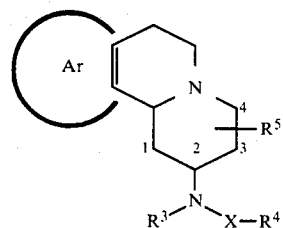

or a pharmaceutical acceptable salt thereof, wherein Ar represents an aromatic heterocycle such as:

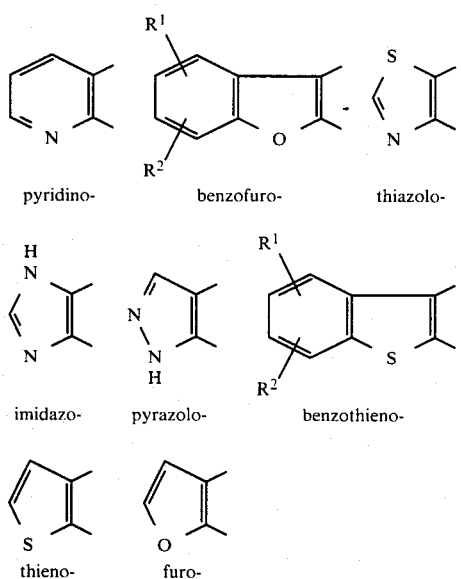

pyridino-   benzofuro-   thiazoloimidazo-   pyrazolo-   benzothienothieno-   furo- $R^1$ and $R^2$ are independently,
(1) hydrogen,
(2) halo, such as chloro, bromo, or fluoro,
(3) hydroxy,
(4) $C_{1-3}$ alkoxy, or
(5) $C_{1-6}$ alkyl, either straight or branched chain;
$R^3$ is
(1) hydrogen,
(2)

wherein R is hydrogen or $C_{1-3}$ alkyl,
(3) $C_{1-6}$ alkyl, either unsubstituted or substituted with one or more of;
 (a) hydroxy,
 (b) carboxy,
 (c) $C_{1-3}$ alkoxycarbonyl,
 (d) halo such as fluoro, chloro or bromo,
 (e) $C_{1-3}$ alkoxy,
 (f) —$CONF^6R^7$ wherein $R^6$ and $R^7$ are the same or different and are hydrogen or $C_{1-5}$ alkyl or joined together either directly to form a 5–7 membered ring such as pyrrolidino, or piperidino, or through a heteroatom selected from N, O, and S, form a 6-membered heterocycle with the nitrogen to which they are attached such as morpholino, piperazino, N-$C_{1-3}$ alkylpiperazino, or
 —$NR^6R^7$ X is

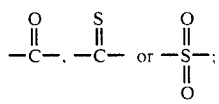

$R^4$ is
 1) —$OR^8$ wherein $R^8$ is hydrogen or $C_{1-6}$ alkyl, either unsubstituted or substituted with one or more of
  (a) —OR, or
  (b) —NRCOR,
 (2) —$N(R^8)_2$ wherein the $R^8$ groups are the same or different.
 (3) —$CO_2R^8$
 (4) —$CONR^6R^7$
 (5) $C_{1-6}$ alkyl, either unsubstituted or substituted with
  (a) $OR^8$
  (b) halo,
  (c) $CO_2R^8$
  (d) $CONR^6R^7$
 (6) $C_{2-5}$ alkenyl,
 (7) $C_{2-5}$ alkenyl,
 (8) $C_{3-6}$ cycloalkyl,
 (9) 5 or 6 membered heterocycle including up to 2 heteroatoms selected from O, N and S, such as imidazo, thiazolo, oxazolo, piperidino, piperazino, pyridino, or pyrazino,
 (10) carbocyclic aryl, of 6 to 10 carbon atoms such as phenyl or naphthyl, either unsubstituted or substituted with one or more of
  (a) halo,
  (b) OR, or
  (c) $C_{1-3}$ alkyl
$R^3$ and $R^4$, taken together directly or through a heteroatom selected from O, N and S, form a 5 or 6-membered heterocycle with the nitrogen to which they are attached such as 2-oxazolidinon-1-yl, or succinimidoyl.
$R^5$ is independently
 (1) $C_{1-6}$ alkyl, either unsubstituted or substituted with one or more of
  (a) —$OR^8$,
  (b) $NR^8COR^8$, or
  (c) $CO_2R^8$,
 (2) —$CO_2R^8$,
 (3) —$CONR^6R^7$;

n is 0, 1, 2 or 3; and
$R^3$ and $R^5$ or $R^4$ and $R^5$, if $R^5$ is in the 1- or 3-position and both are alkyl, can be joined together to form a 5- or 6-membered ring.

The pharmaceutically acceptable salts coming within the purview of this invention include the pharmaceutically acceptable acid addition salts. Acids useful for preparing these acid addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic, theophylline, 8-chlorotheophylline, p-aminobenzoic, p-acetamidobenzoic, methanesulfonic, or ethanedisulfonic acid.

In a preferred embodiment of this invention, Ar is $R^1,R^2$-benzo[b]furo- or $R^1,R^2$-benzo[b]-thieno. It is further preferred that $R^1$ and $R^2$ be hydrogen or halo and $R^3$ be $C_{1-6}$ alkyl, especially methyl, and that $R^4$ be $C_{1-6}$ alkyl, di($C_{1-3}$ alkyl)amino, halo-$C_{1-6}$ alkyl, hydroxy-$C_{1-6}$ alkyl, $C_{2-5}$ alkenyl, carbocyclic aryl, 5 or 6-membered heterocycle, —$CO_2R^8$, $C_{1-6}$ alkyl-$CO_2R^8$ or —$C_{1-6}$ alkyl-$CONR^6R^7$. It is also preferred that $R^5$ be hydrogen or $C_{1-6}$ alkyl and that X be —$SO_2$—.

It is most preferred that $R^1$ and $R^2$ be hydrogen, $R^3$ be methyl, $R^4$ be $C_{1-6}$ alkyl, hydroxypropyl, hydroxyethyl, dimethylamino, $C_{1-3}$ alkoxycarbonylethyl, or dimethylaminocarbonylmethyl, and $R^5$ be hydrogen.

These compounds are depicted as having the configuration in which the hydrogen at C-12b and the nitrogen at C-2 are trans

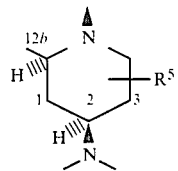

and it is the more preferred isomer for $\alpha_2$-adrenoceptor blockade activity. However, the isomers having the configuration in which the hydrogen at C-12b and the nitrogen at C-2 are cis are also active $\alpha_2$-adrenoceptor blockers and are considered to be within the scope of this invention. Each of the 2RS,12bSR and 2RS,12bRS-configurational isomers are racemates capable of being resolved into dextrorotatory and levorotatory enantiomers. This invention includes these pure enantiomers as well as all mixtures thereof, especially the racemates.

A process for preparing the compounds of this invention comprises acylation (carboxyl or sulfonyl) of the compound of structure IIa:

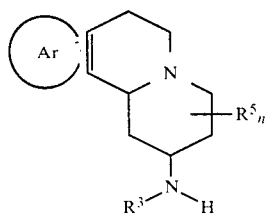

with an acylating reagent such as an acid anhydride, activated ester, mixed acid anhydride or acid halide capable of introducing a substituent of formula —XR⁴, and preferably wherein the reagent is of structure:

wherein halo is chloro, bromo or iodo, preferably chloro, and X is

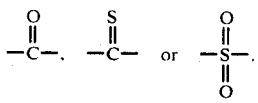

The reaction is conducted in an inert solvent such as a chlorinated hydrocarbon, e.g., methylene chloride, chloroform, 1,2-dichloroethane or the like in the presence of an acid acceptor such as triethylamine, pyridine, an alkali metal carbonate, or basic anion exchange resin. The reaction usually proceeds readily at about room temperature but any temperature from about 0° C. to the boiling point of the reaction mixture is reasonable depending on the reactivity of the particular acyl halide and temperature. Reaction times of about half an hour to about 48 hours are required, and in most cases about one to 18 hours suffices.

In those compounds wherein —XR⁴ is a carbamoyl or thiocarbamoyl group such as

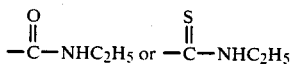

an alternative novel process comprises treatment of compound IIa with the appropriate alkyl isocyanate or isothiocyanate respectively. The synthesis is conducted in an inert organic solvent or lower alkanol such as ethanol, propanol, 1,2-dimethoxyethane or the like at about room temperature (20° C.) to 100° C. for about 5 minutes to about 2 hours.

The process for the preparation of the compound wherein R³ and XR⁴ are joined together to form the sultam or lactam substructure:

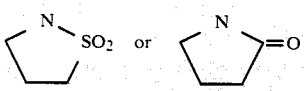

comprises treating the compound with substructure

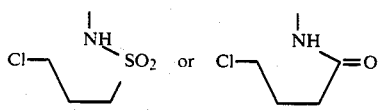

with a strong base such as potassium t-butoxide, n-butyl lithium, sodium hydride or the like in an ethereal solvent such as 1,2-dimethoxyethane, diglyme, THF or the like at about 20° C. to 60° C. for about one to 5 hours.

The process for preparing compounds with an imide substructure in the 2-position such as

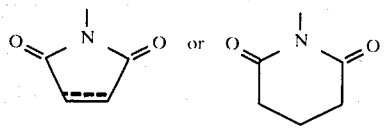

comprises heating compound IIa wherein R³ is hydrogen with the corresponding cyclic dicarboxylic anhydride of structure:

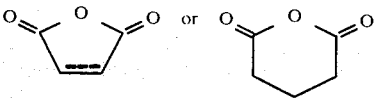

respectively in an inert solvent such as toluene or with no solvent at about 100° to 150° C. for about 2 to 5 hours.

The compounds with a cyclic carbamate, cyclic urea or cyclic sulfamide in the 2-position of structures:

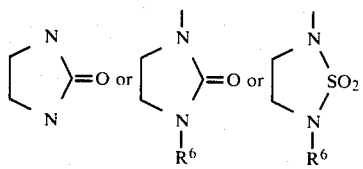

are prepared by treating the compound with substructure:

IIb

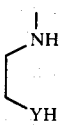

wherein Y is —O— or NR⁶ with carbonyl diimidazole or sulfuryl chloride in an inert solvent such as dimethoxyethane, methylene chloride or the like at about 20° to 60° C. in the presence of an acid acceptor such as triethylamine, di(isopropyl)ethylamine or the like for about 5 to 18 hours.

In the novel method of selectively antagonizing α₂-adrenergic receptors in a patient, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

These doses are useful for treating colonic spasm irritable bowel syndrome and constipation.

The compounds, or pharmaceutically acceptable salts thereof, of the present invention, in the described dosages, are administered orally, intraperitoneally, subcutaneously, intramuscularly, transdermally or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

(2SR,12bRS)-N-(1,3,4,6,7,12b-Hexahydro-2H-benzo[b]-furo[2,3-a]quinolizin-2-yl)-N,N',N'-trimethylsulfamide

Step A: Preparation of 3-Cyanomethylbenzo[b]furan

To a suspension of 2.64 gms (0.11 mole) of oil free sodium hydride in 200 ml of tetrahydrofuran (THF) was added dropwise a solution of 19.47 gms (0.11 mole) of diethylcyanomethylphosphonate in 75 mL of THF. After the $H_2$ evolution had ceased, a solution of 13.4 g (0.1 mole) of 3-(2H)-benzo[b]-furanone in 100 mL of THF was added. The solution was heated at 70° C. for 1.5 hrs, cooled, and poured into 500 mL of 5% HCl, and washed with ether. The ether phase was washed with brine, dried ($MgSO_4$), filtered and concentrated to give 15.4 g of a dark oil. The product was distilled at 96°-100° C./0.075 mm Hg to give 10.85 g of a yellow oil which crystallized upon standing.

Step B: Preparation of 2-(3-benzo[b]furanyl)ethylamine

A solution of 3.97 g (0.025 mole) of 3-cyanomethyl-benzo[b]furan in 200 mL of diethyl ether was slowly added to a refluxing suspension of 3.84 g (0.1 mole) of lithium aluminum hydride in 400 mL of ether. The reaction was heated 3 hrs., cooled and water was slowly added. The suspension was filtered through a pad of filter aid and the filtrate was evaporated to give 3.2 g of oily product. The hydrochloride salt has m.p. 183°–185° C.

Step C: Preparation of 3-(2-Formamidoethyl)benzo[b]furan

A solution of 2.35 g (0.015 mole) of 2-(3-benzo[b-]furanyl)ethylamine and 5 mL of ethyl formate was heated at 60° C. for 3 hours, poured into 2N HCl and washed with methylene chloride which in turn was washed with 5% sodium hydroxide (w/v), dried ($MgSO_4$), filtered and concentrated to give 2.70 g of product.

Step D: Preparation of 3,4-dihydrobenzo[b]furo[2,3-c]pyridine 2.28 Grams (0.012 mole) of 3-(2-formamidoethyl)benzo[b]furan was added to 28 g of polyphosphoric acid which was preheated to 100° C. After 1–1.5 hours, the reaction mixture was poured onto ice and the residues were washed with water. The polyphosphoric acid was dissolved in water, filtered through a pad of celite and made basic with concentrated ammonia. A precipitate was collected and dried to give 1.45 g of product, m.p. 170°–171° C.

Step E: Preparation of (12bRS)-1,3,4,6,7,12b-Hexahydrobenzo[b]furo[2,3a]-guinolizin-2-one To a solution of 12 g (0.070 mol) of 3,4-dihydrobenzo[b]furo [2,3-c]pyridine dissolved in 500 mL of acetonitrile at 60° C. was added 20 g (0.140 mol) of 2-trimethylsiloxy-1,3-butadiene followed by 13.6 g (0.10 mol) of anhydrous zinc chloride. The mixture was heated at 60° C. for 1.5 hour, cooled to 25° C., and 30 mL of 5% HCl was added and stirred 10 minutes. 40% Sodium hydroxide was added until the reaction was basic; 200 mL of water was added; and the acetonitrile layer was separated. The aqueous layer was filtered through celite and washed with ether. The combined organic layers were dried ($Na_2SO_4$), filtered, and concentrated to a brown residue which was chromatographed (silica, ethyl acetate/hexane (1:1)) to give 8.2 g of product, m.p. 108°–9° C.

Resolution of (12bSR)-1,3,4,6,7,12b-hexahydrobenzo-[b]furo[2,3-a]quinolizin-2-one A solution of (−)-di-p-toluoyl-L-tartaric acid monohydrate (25.9 g) in 100 ml of ethyl acetate was mixed with a solution of (12bSR)-1,3,4,6,7,12b-hexahydrobenzo[b]furo[2,3-a]quinolizin-2-one (15.5 g) in 700 ml of ethyl acetate and allowed to stand 12–78 hours. The mixture was filtered to yield 21 g of the di-p-toluoyl-L-tartrate salt of the amine. The free base was liberated by partitioning between aqueous $Na_2CO_3$ and ethyl acetate ($[\alpha]_D$=ca. −79° ; C=0.001,; $CHCl_3$). The diasteriomeric salt of this material was again prepared following the above procedure. The collected di-p-toluoyl-L-tartrate salt was partitioned between ethyl acetate and aqueous $Na_2CO_3$, dried ($Na_2SO_4$), filtered, treated with charcoal, filtered and evaporated to yield 5.4 g (35%) of (12bS)-1,3,4,6,7,12b-hexahydrobenzo[b]furo[2,3-a]quinolizin-2-one; $[\alpha]_D$= −84° ; (C=0.001, $CHCl_3$).

The (12bR)-1,3,4,6,7,12b-hexahydrobenzo[b]furo[2,3-a]quinolizin-2-one was obtained by substituting (+)-di-p-toluoyl-D-tartaric acid monohydrate for (−)-di-p-toluoyl-L-tartaric acid in the above procedure to provide product with $[\alpha]_D$= +84° (C=0.001, $CHCl_3$).

Employing the procedures substantially as described in Example 1, Steps A through E, or in some cases, Steps C through E but substituting for the 3-benzofuranone used in Step A thereof the ketones described in Table I, or for the ethylamines used in Step C thereof, the corresponding ethylamines described in Table I, or for the butadienes used in Step E thereof, the corresponding substituted butadienes described in Table I, there are prepared the Ar[2,3-a]quinolizin-2-ones, also described in Table I by the following reactions:

TABLE I

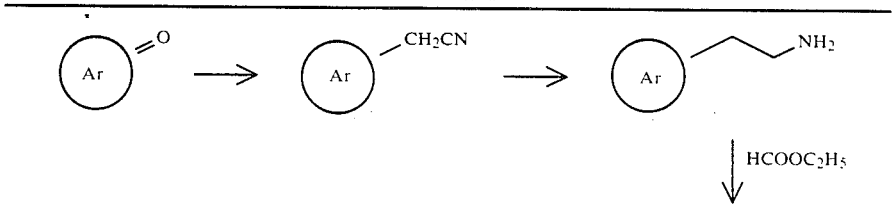

TABLE I-continued

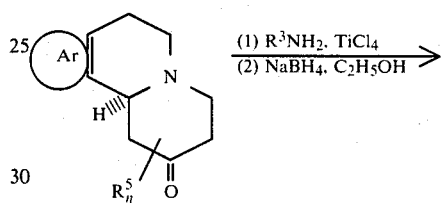

| Ar | $R_n^5$ | Ar | $R_n^5$ |
|---|---|---|---|
| 10-chlorobenzo[b]furo- | H | benzo[b]thieno- | 1-CH₃ |
| thieno- | H | 10-methylbenzo[b]thieno- | 4-COOCH₃ |
| furo- | 3-CH₃ | 9-methoxybenzo[b]thieno- | H |
| 11-hydroxybenzo[b]furo | H | 11-fluorobenzo[b]furo- | H |
| 10,11-dimethylbenzo[b]furo- | H | 9-bromobenzo[b]furo- | 1-CON(CH₃)₂ |
|  |  | 11-methoxybenzo[b]furo- | H |
| benzo[b]furo- | 1,4-CH₃ | benzo[b]furo- | 1,3-CH₃ |
| benzo[b]furo- | 4-CH₃ |  |  |

Step F: Preparation of (2SR12bRS)-N-(1,3,4,6,7,12b-hexahydro-2H-benzo[b]furo[2,3-a]quinolizin-2-yl)-N-methylamine To a solution of 2.41 g (0.010 mol) of (12bRS)-1,3,4,6,7,12b-hexahydrobenzo[b]furo[2,3-a]quinolizin-2-one dissolved in 60 mL of ether and 40 mL of benzene cooled to 0° C. was added 5 mL of methylamine followed by a solution of 0.56 mL (0.052 mol) of titanium tetrachloride in 3 mL of benzene. The reaction was stirred at 0° C. for 30 minutes, warmed to 25° C. and stirred 2 hours. The mixture was filtered through a pad of celite, and the salts were washed with benzene/ether (2:1). The filtrate was evaporated, giving 2.55 g of an oil. The oil was dissolved in 80 mL of ethanol and 0.38 g (0.010 mol) of sodium borohydride was added. The solution was stirred 18 hours, and 100 mL of water was added. Stirring was continued for 30 minutes; the ethanol was evaporated in vacuo and the aqueous phase was extracted with methylene chloride which was dried (Na₂SO₄), filtered, and concentrated, giving 2.56 g of product. The product was purified by chromatography (silica gel, chloroform saturated with NH₃) to yield 1.77 g of product. The dihydrochloride salt obtained from ethanolic HCl has m.p. 300° C.

Employing the procedures described in Step F hereof but starting with the substantially enantiomerically pure quinolizin-2-ones from Step E there were produced: (2R,12bS)-N-(1,3,4,6,7,12b-hexahydro-2H-benzo[b]furo-[2,3-a]quinolizin-2-yl)-N-methylamine, m.p. 77°–79° C., [α]₅₈₉ −66° (CHCl₃); and (2S,12bR)-N-(1,3,4,6,7,12b-hexahydro-2H-benzo[b]furo-[2,3-a]quinolizin-2-yl)-N-methylamine, m.p. 77°–79° C., [α]₅₈₉ −66° (CHCl₃).

Employing the procedure substantially as described in Example 1, Step F but substituting for the intermediates and reagents used therein, the Ar[2,3-a]quinolizin-2-ones and the amines of structure R³NH₂, described in Table II, there are prepared the N-(Ar[2,3-a]quinolizin-2β-yl)-N-R³-amines, also described in Table II by the following reaction.

TABLE II

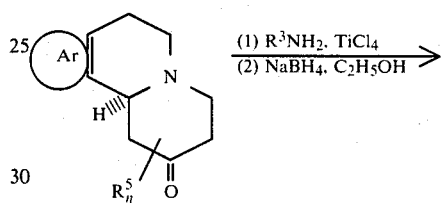

(1) R³NH₂, TiCl₄
(2) NaBH₄, C₂H₅OH

| Ar | $R^3$ | $R_n^5$ |
|---|---|---|
| 11-fluorobenzo[b]furo- | CH₃— | H |
| thieno- | n-C₃H₇— | H |
| furo- | (CH₃)₂NCOCH₂— | 1-CH₃ |
| 11-hydroxybenzo[b]furo- | CH₃— | H |
| 10,11-dimethylbenzo[b]furo- | CH₃NHC₂H₄— | 3-COOCH₃ |
| benzo[b]thieno- | CH₃OCH₂CH₂— | H |
| 10-methylbenzo[b]thieno- | CH₃— | H |
| 9-methoxylbenzo[b]thieno- | C₂H₅— | 4-CON(Me)₂ |
| 10-chlorobeno[b]thieno- | C₂H₅O₂CCH₂— | H |
| 9-bromobenzo[b]furo- | H— | 4-CH₃ |
| 11-methoxybenzo[b]furo- | C₂H₅— | H |
| benzo[b]furo- | HOC₂H₄— | 3-CH₃ |
| benzo[b]furo- | n-C₃H₇— | H |
| benzo[b]furo- | H₂NOCH₂C— | H |
| benzo[b]furo- | CH₃CO— | 1-COOCH₃ |
| benzo[b]furo- | ClCH₂CH₂CH₂— | H |
| benzo[b]furo- | CH₃ | 1,4-CH₃ |
| benzo[b]furo- | CH₃ | 1,3-CH₃ |

Step G: Preparation of (2SR,12bRS)-N-(1,3,4,6,7,12b-hexahydro-2H-benzo[b]furo[2,3-a]quinolizin-2-yl)-N,N′,N′-trimethylsulfamide HCl To a solution of 2.54 g (0.01 mol) of amine from Step F in 50 mL of methylene chloride was added 2.00 g (0.020 mol) of triethylamine followed by 2.80 g (0.02 mol) of dimethylsulfamoyl chloride. The mixture was stirred for 36–48 hours and then poured into 100 mL of 5% (w/v) NaOH which was then extracted with methylene chloride. The organic layer was dried (Na$_2$SO$_4$), filtered and concentrated to give 3.75 g of an oil which was chromatographed (silica/2% CH$_3$OH/CHCl$_3$) to give 2.92 g of product. The free base was acidified with ethanolic HCl. Addition of ether afforded the hydrochloride, m.p. 256°–257° C.

Employing the procedure substantially as described in Example 1, Step G but substituting for the racemic amine from Step F equal amounts of the substantially enantiomerically pure amines there were produced the (2R,12bS)-trimethylsulfamide; [α]$_{589}^{20}$ (free base) +17° (C=0.001, pyridine); m.p. (HCl salt) 263°–264° C.; and (2S,12bR)-N-1,3,4,6,7,12b-hexahydro-2H-benzo[b]furo[2,3-a]quinolizin-2-yl)-N,N',N'-trimethylsulfamide; [α]$_{589}^{20}$ (free base) -17° (C=0.001, pyridine); m.p. (HCl salt) 263°–264° C.

Employing the procedure substantially as described in Example 1, Step G, but substituting for the dimethylsulfamoyl chloride and the amine used therein comparable amounts of the compounds R$^4$-X-Cl and the amines described in Table III there are produced the (R$^3$)(R$^4$X) amines, also described in Table III, in accordance with the following reaction:

TABLE III

| (Ar) | R$^3$ | X | R$^4$ | R$^5{}_n$ | Reaction time (Hrs) | Salt mp (°C.) |
|---|---|---|---|---|---|---|
| benzo[b]furo | —CH$_3$ | —SO$_2$— | —CH$_2$CH(CH$_3$)$_2$ | H | 3 | HCl, 237–239 |
| benzo[b]furo | —CH$_3$ | —CO— | —CH$_2$CH$_3$ | H | 1 | HCl, 1.5H$_2$O 165–170 |
| benzo[b]furo | —CH$_3$ | —CO— | —CH$_2$CH(CH$_3$)$_2$ | H | 1 | HCl, 0.5H$_2$O 223–226 |
| benzo[b]furo | —CH$_3$ | —CO— | —C(O)—OCH$_3$ | H | 1 | HCl, 0.25H$_2$O 204–206 |
| benzo[b]furo | —CH$_3$ | —CO— | —N(CH$_3$)$_2$ | H | 48 | HCl, 0.75 H$_2$O 174–177 |
| benzo[b]furo | —CH$_3$ | —CO— | —OC$_2$H$_5$ | H | 0.5 | HCl, 0.75H$_2$O 240–243 |
| benzo[b]furo | —CH$_3$ | —CO— | —C(O)—OC$_2$H$_5$ | H | 18 | HCl, 225 |
| (2R,12bS)benzo-[b]furo | —CH$_3$ | —SO$_2$ | —CH$_2$Cl | H | 18 | HCl, 168–170 |
| benzo[b]furo | —CH$_3$ | —CO— | furyl | H | 1.5 | HCl, 0.5H$_2$O 275–280 |
| benzo[b]furo | —CH$_3$ | —SO$_2$— | pyridyl | H | 18 | HCl, 250 |
| benzo[b]furo | —CH$_3$ | —CO— | phenyl | H | 18 | HCl, 0.5H$_2$O 250 |
| benzo[b]furo | —CH$_3$ | —CO— | dioxolane-CH$_2$O— | H | | |
| benzo[b]furo | —CH$_3$ | —SO$_2$— | CH$_2$CH$_2$OH | H | | HCl, 250 |

TABLE III-continued

| Ar | R³ | X | R⁴ | R⁵ₙ | Reaction time (Hrs) | Salt mp (°C.) |
|---|---|---|---|---|---|---|
| benzo[b]furo | —CH₃ | —CO— | —CO—N(CH₃)₂ | H | | HCl, 325 |
| benzo[b]furo | HOCH₂CH₂— | —SO₂ | —N(CH₃)₂ | H | | HCl, 0.5H₂O |
| benzo[b]furo | —CH₃ | —SO₂ | CH₂CH=CH₂ (allyl) | H | | HCl, 0.5H₂O 248 |
| benzo[b]furo | —CH₃ | —SO₂— | C₂H₅— | H | | HCl, 257–260 |
| benzo[b]furo | n-C₃H₇ | —SO₂ | —N(CH₃)₂ | H | | HCl, 160 |
| benzo[b]furo | —CH₃ | —SO₂— | CH₂CH₂COOCH₃ | H | | HCl, 227–28 |
| benzo[b]furo | —CH₃ | —CO— | CH₂COOC₂H₅ | H | | HCl, 202–04 |
| benzo[b]furo | —CH₃ | —CO— | CH₂OCH₃ | H | | HCl, 227–28 |
| benzo[b]furo | —CH₂CONH₂ | —SO₂— | —N(CH₃)₂ | H | | HCl, 1.5H₂O; 225–227 |
| benzo[b]furo | CH₃— | —SO₂— | CH₂CH₂CH₂Cl | H | | HCl, 234–236 |
| benzo[b]furo | CH₃— | —CO— | CO—N(pyrrolidinyl) | H | | HCl, 240–243 |
| benzo[b]furo | CH₃— | —SO₂— | 2-furyl | H | | HCl, 270–275 |
| benzo[b]thieno | CH₃— | —SO₂— | C₂H₅ | H | | HCl, 240 |
| benzo[b]furo | CH₃— | —SO₂— | 2-thienyl | H | | HCl, 270 |
| benzo[b]furo | CH₃— | —SO₂— | CH₂COOC₂H₅ | H | | HCl, 0.5H₂O; 147–150 |
| benzo[b]furo | CH₃— | —SO₂— | 2-thiazolyl | H | | HCl; 260 |
| 11-fluorobenzo[b]furo | CH₃— | —SO₂ | cyclopentyl | 3-CH₃ | | |
| 11-methoxybenzo[b]furo | C₂H₅— | —SO₂— | 4-(S-oxo-thiomorpholinyl) | 4-CH₃ | | |
| benzo[b]thieno | CH₃— | —CO— | pyrazinyl | H | | |

TABLE III-continued

| Ar | R³ | X | R⁴ | R⁵$_n$ | Reaction time (Hrs) | Salt mp (°C.) |
|---|---|---|---|---|---|---|
| benzo[b]furo- | CH₃— | —SO₂— | CH₃ | 1,4-CH₃ | | |
| benzo[b]furo | CH₃— | —SO₂— | CH₃ | 1,3-CH₃ | | |
| benzo[b]furo | CH₃— | —SO₂— | —CH₂CON(CH₃)(CH₃) | H | | HCl, 0.5H₂O 151–153 |
| benzo[b]furo | —CH₃ | —CO— | 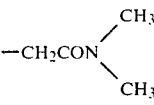 | H | 12 | 2HCl, 280–284 |
| benzo[b]furo | —CH₃ | —SO₂— | 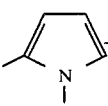 | H | 16 | HCl, 290–294 |
| 10-chlorobenzo-[b]furo | —CH₃ | —SO₂— | —C₂H₅— | H | 14 | HCl, 262–264 |
| benzo[b]furo | —CH₃ | —CO— | | H | 3 | HCl, 305–310 |
| benzo[b]furo | —CH₃ | —SO₂— | —CH₃ | H | 4 | HCl, 255(dec) |
| (2R,12bS)benzo-[b]furo | —CH₃ | —SO₂— | 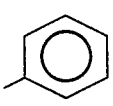 | H | 18 | HCl, 263–264 |
| benzo[b]furo | —CH₃ | —SO₂— | —CH₂Ph | H | 8 | HCl, 255–265 |
| 11-methoxybenzo-[b]furo | —CH₃ | —SO₂— | —Et | H | 10 | HCl, 244–247 |
| (2S,12bR)benzo-[b]furo | —CH₃ | —SO₂— | 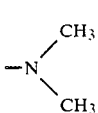 | H | 18 | HCl, 263–264 |
| benzo[b]thieno | —CH₃ | —SO₂— | —CH₂CH₂OH | H | 2 | HCl, 0.5H₂O 164–167 |
| benzo[b]thieno | —CH₃ | —SO₂— | —CH₃ | H | 4 | HCl, 250 |
| 11-chlorobenzo-[b]furo | —CH₃ | —SO₂— | —C₂H₅— | H | 3 | HCl, 0.5H₂O, 256–259 |
| benzo[b]thieno | —CH₃ | —SO₂— | 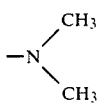 | H | 18 | HCl, 265–268 |
| 9-chlorobenzo-[b]furo | —CH₃ | —SO₂— | —C₂H₅— | H | 4 | HCl, 280 |
| (2S,12bR)benzo-[b]furo | —CH₃ | —SO₂— | —CH₂CH₂OH | H | 1 | HCl, 265(dec) |
| (2R,12bS)benzo-[b]furo | —CH₃ | —SO₂— | —CH₂CH₂OH | H | 1 | HCl, 265(dec) |
| (2R,12bS)benzo-[b]furo | —CH₃ | —SO₂— | —CH₃ | H | 1 | HCl, 280–284 |
| benzo[b]furo | —CH₃ | —SO₂— | —N(H)— | H | 18 | HCl, 225–227 |
| benzo[b]furo | —CH₃ | —SO₂— | 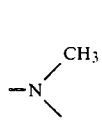 | H | 24 | HCl, 0.5H₂O 214–216 |
| 9-methoxybenzo-[b]furo | —CH₃ | —SO₂— | —C₂H₅— | H | 5 | HCl, 231–234 |
| 10-methoxybenzo-[b]furo | —CH₃ | —SO₂— | —C₂H₅ | H | 4 | HCl, H₂O, 240–242 |
| 9-methoxybenzo-[b]furo | —CH₃ | —SO₂— | —N(CH₃)₂ | H | 18 | HCl, .75H₂O, 234–236 |

TABLE III-continued

| Ar | R³ | X | R⁴ | R⁵ₙ | Reaction time (Hrs) | Salt mp (°C.) |
|---|---|---|---|---|---|---|
| 10-methoxybenzo-[b]furo | —CH₃ | —SO₂— | —N(CH₃)₂ | H | 18 | HCl, 247–248 |
| thieno | —CH₃ | —SO₂— | —N(CH₃)₂ | H | 18 | HCl, 0.25H₂O, 243–245(dec) |
| benzo[b]furo | —CH₃ | —SO₂— | —N(CH₂CH₂OH)₂ | H | 24 | 0.5H₂O, 140–142 |
| thieno | —CH₃ | —SO₂— | —C₂H₅ | H | 8 | HCl, H₂O, 247–250 |
| 10-chlorobenzo-[b]furo | —CH₃ | —SO₂— | —N(CH₃)₂ | H | 16 | HCl, 0.25H₂O |
| 10-methylbenzo-[b]thieno | —CH₃ | —SO₂— | —C₂H₅ | H | 6 | HCl, 280 |
| 11-chlorobenzo-[b]thieno | —CH₃ | —SO₂— | —C₂H₅ | H | 4 | HCl, 278–281 |
| 11-chlorobenzo-[b]thieno | —CH₃ | —SO₂— | —N(CH₃)₂ | H | 18 | HCl, 246–248 |
| 9-hydroxybenzo-[b]furo | —CH₃ | —SO₂— | —C₂H₅ | H | 3 | HCl, 301–304 |
| 11-Isopropyl-benzo[b]thieno | —CH₃ | —SO₂— | —C₂H₅ | H | 6 | HCl, 228–230 |
| benzo[b]furo | —CH₃ | —SO₂— | —CH₃ | 1@-CH₃ | 2 | HCl, 0.25H₂O; 270–273 |
| benzo[b]furo | —CH₃ | —SO₂— | —CH₃ | 3@-CH₃ | 2 | HCl, 0.25H₂O; 262–264 |
| benzo[b]furo | —CH₃ | —SO₂— | —CH₃ | 1β-CH₃ | 2 | HCl, 0.5H₂O; 250–252 |
| benzo[b]furo | CH₃— | —SO₂— | —N⌒N—CH₃ (N-methylpiperazine) | 1-CH₃ | | |
| 9-methoxybenzo-[b]thieno | C₂H₅ | —CO— | —CH₂CH₂CH₂—NH₂ | 3-C₂H₅ | | |
| thieno- | n-C₃H₇ | —SO₂— | (pent-2-ynyl) | 1-C₃H₇ | | |
| furo- | (CH₃)NCOCH₂— | —SO₂— | (2-naphthyl) | H | | |
| 11-hydroxybenzo-[b]furo | CH₃— | —SO₂— | (4-chlorophenyl) | 4-COOCH₃ | | |
| 10,11-dimethyl-benzo[b]furo- | CH₃NHC₂H₄ | —SO₂— | (4-hydroxyphenyl) | H | | |
| 10-methylbenzo-[b]thieno- | CH₃— | —SO₂— | (3-methoxyphenyl) | 1-COOCH₃ | | |
| 10-chlorobenzo-[b]thieno- | —C₂H₅CO₂CH₃ | —SO₂— | —CH₃ | H | | |
| 9-bromobenzo-[b]furo- | H— | —SO₂— | —C₂H₅ | H | | |
| benzo[b]furo | CH₃CO— | —SO₂— | —CH₂C(O)N(CH₃)₂ | 3-CH₂Ph | | |
| benzo[b]furo | Cl(CH₂)₃— | —SO₂— | n-C₃H₇ | H | | |

TABLE III-continued

| Ar | R³ | X | R⁴ | R⁵ₙ | Reaction time (Hrs) | Salt mp (°C.) |
|---|---|---|---|---|---|---|
| benzo[b]furo | —CH₃ | —CO— | —CH₂—CH₂— | | | |
| benzo[b]furo | —CH₃ | —SO₂— | —CH₂ | | | |

EXAMPLE 2

(2SR,12bRS)-N-(1,3,4,6,7,12b-hexahydro-2H-benzo[b]-furo[2,3-a]quinolizin-2-yl)-N-methyl-2-hydroxyethanesulfonamide Solutions of 2-hydroxyethanesulfonyl chloride (20.2 g; 0.14 mol) in 100 ml of acetonitrile and triethylamine (14.3 g; 19.7 ml; 0.14 mol) in 100 ml of methylene chloride were added simultaneously by means of a dual syringe drive to a solution of amine from Step F of Example 1 (17.9 g; 0.07 mol) in 1600 ml of a 1:1 mixture of acetonitrile and methylene chloride. After 15 minutes, the solvent was evaporated and the residue was partitioned between methylene chloride and water. The organic phase was separated and washed with water, brine and dried (Na₂SO₄). The solvent was evaporated and the residue was chromatographed over silica gel (CHCl₃ saturated with NH₃). The product obtained (14 g; 55%) was converted to give the product as the hydrochloride salt; m.p. 250° C. (dec).

By employing the procedure substantially as described above but substituting for racemic amine from Step F equal amounts of the enantiomerically pure amines there were produced the hydrochloride salts of the (2R,12bS)-sulfonamide, m.p. 265° C., [α]₅₈₉+13° (C=0.001; CH₃OH); and the (2S,12bR)-sulfonamide, m.p. 265° C. [α]₅₈₉−13° (C=0.001;CH₃OH) sulfonamide.

EXAMPLE 3

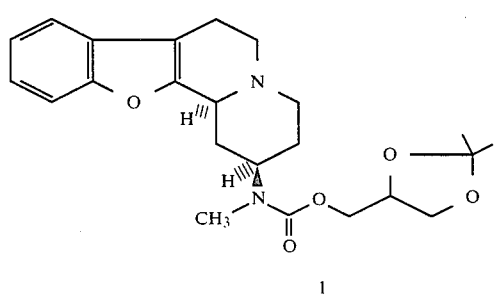

1

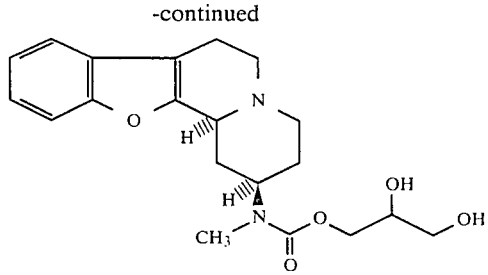

2

(2SR,12bRS)-1-(2,3-Dihydroxypropyl)-N-(1,3,4,6,7,12b-hexahydro-2H-benzo[b]furo2,3-a]quinolizin-2-yl)-N-methyl-carbamate oxalate The carbamate, 1 (0.324 g, 0.723 mmole) was dissolved in 5 mL of acetone and 5 mL of 3N HCl and was stirred at room temperature for 30 minutes; made basic with 40% NaOH; and was extracted with methvlene chloride. The extract was dried, filtered and concentrated. The crude oil obtained was purified by spinning plate chromatography (NH₃ sat'd CHCl₃) to give 0.185 g of product (63%). The monoxalate salt has m.p. 83°–86° C.

EXAMPLE 4

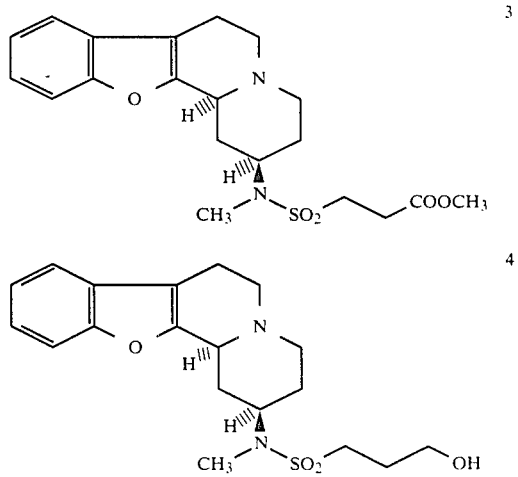

(2SR,12bRS)-N-(1,3,4,6,7,12b-Hexahydro-2H-benzo[b]-furo[2,3-a]quinolizin-2-yl)-N-methyl-3-hydroxypropanesulfonamide.hydrochloride, 4

To the ester, 3, (0.130 g, 0.32 mmole) dissolved in 10 mL of ether at 0° C. was added 0.016 g (0.42 mmole) of lithium aluminum hydride. After 30 minutes, the reaction was poured into dilute HCl and made basic with 40% NaOH. The aqueous solution was extracted with methylene chloride and the extract was dried, filtered and concentrated to an oil. The oil was chromatographed on a spinning plate (2% acetone/ethyl acetate) to give 0.100 g of product (82%). The HCl salt has m.p. 239°–241° C.

EXAMPLE 5

Preparation of (2SR,12bRS)-2-[N'-(1,3,4,6,7,12b-Hexahydro-2H-benzo[b]furo[2,3-a]quinolizin-2-yl)-N'-methylaminosulfonyl]N,N-dimethyl acetamide hychochloride hemihydrate Dimethylamine hydrochloride (0.222 g, 2.72 mmole) was slurried in 20 mL of dry benzene and cooled to 0° C. To this was added 1.36 mL (2.72 mmol) of 2N trimethyl aluminum in toluene. After stirring at room temperature for 1.5 hours, 0.275 g (0.68 mmol) of (2RS,12bSR)-ethyl 2-([N-(1,3,4,6,7,12b-hexahydro-2H-benzo[b]furo[2,3-a]quinolizin-2-yl)-N-methylamino-sulfonyl]acetate was added dropwise in 2 mL of benzene. After refluxing 18 hour, the reaction was cooled and 1N HCl was added until gas evolution ceased. The mixture was made alkaline with solid Na₂CO₃, filtered through a filter pad, and washed with 25 ml of ethyl acetate. The layers were separated and the aqueous layer was extracted with 3×10 mL of ethyl acetate. The organic fractions were combined, washed with water and saturated sodium chloride, dried (Na₂SO₄) and evaporated to dryness. Medium pressure column chromatography over silica gel, eluting with ethyl acetate gave 0.06 g (0.15 mmol) of starting ester. Continued elution with 5% (v/v) CH30H/CHCl₃ afforded 0.136 g (0.33 mmol) of the dimethyl acetamide in 62.2% yield based on ester consumed. This was dissolved in ether and ethanolic HCl was added dropwise to give a white solid, m.p., 151°–153° C. (acetone/hexane).

EXAMPLE 6

(2SR,12bRS)-N-(1,3,4,6,7,12b-Hexahydro-2H-benzo[b]-furo[2,3-a]quinolizin-2-yl)-N-methyl-N'-ethylurea.HCl.H₂O 0.100 Grams (0.39 mmol) of (2SR,12bRS)-N-(1,3,4,6,7,12b-hexahydro-2H-benzo[b]furo-[2,3-a]-quinolizin-2-yl)-N-methylamine was dissolved in 3 mL of ethanol and 0.5 mL of ethyl isocyanoate. The reactants were heated to 60° C. for 10 minutes and then evaporated to dryness to give 0.110 g of product. The hydrochloride salt monohydrate melts at m.p. 199°–202° C.

Employing the procedure substantially as described in Example 6 but substituting for the amine and the ethyl isocyanate used therein, the amines and isocyanates described in Table IV there are produced the ureas, also described in Table IV, by the following reaction:

TABLE IV

| (Ar) | R³ | R⁶ |
|---|---|---|
| benzo[b]furo- | —CH₃ | t-C₄H₉— |
| 11-methoxybenzo[b]furo- | —C₂H₅ | CH₃— |
| benzo[b]thieno- | —CH₃ | iso-C₂H₇— |
| 11-chlorobenzo[b]furo- | —CH₃ | C₂H₅— |

EXAMPLE 7

(2SR,12bRS)-N-(1,3,4,6,7,12b-Hexahydro-2H-benzo[b]-furo[2,3-a]quinolizin-2-yl)-N-methyl-N'-ethylthiourea.HCl.0.5 H₂O 0.100 Grams (0.39 mmol) of amine from Example 1, Step F is dissolved in 3 mL of dimethoxyethane and 0.5 mL of ethyl isothiocyanate. After 20 minutes, the reaction is evaporated to give the product (0.110 g). The hydrochloride salt hemihydrate melts at 199°–201°C.

Employing the procedure substantially as described in Example 7 but substituting for the amine and the ethylisothiocyanate used therein, the amines and isocyanates described in Table V there are produced the thioureas, also described in Table V, by the following reaction:

TABLE V

| (Ar) | R³ | R⁶ |
|---|---|---|
| benzo[b]furo- | CH₃— | t-C₄H₉— |

TABLE V-continued

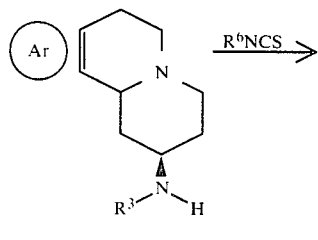

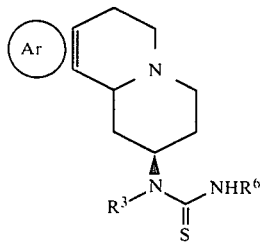

| Ar | R³ | R⁶ |
|---|---|---|
| benzo[b]furo- | n-C₃H₇— | C₂H₅— |
| benzo[b]thieno- | CH₃— | CH₃— |
| 10-chlorobenzo[b]thieno-furo- | C₂H₅O₂CCH₂— | iso-C₃H₇— |
| | (CH₃)₂NCOCH₂— | CH₃— |

EXAMPLE 8

(2SR,12bRS)-N-(1,3,4,6,7,12b-Hexahydro-2H-benzo[b]-furo[2,3-a]quinolizin-2-yl)-2-methylpropane sulfonamide.HCl Step A: Preparation of (2SR,12bRS)-N-(1,3,4,6,7,12b-hexahydro-2H-benzo[b-]furo[2,3-a]quinolizin-2-yl)-amine To a solution of (2SR)-1,3,4,6,7,12b-hexahydrobenzo[b]furo[2,3-a]quinolizin-2-one (0.10 g, 0.41 mmol) in 5 mL of methanol was added 0.224 g (2.9 mmol) of ammonium acetate and 0.027 g (0.41 mmol) of sodium cyanoborohydride. The reaction was stirred at 25° C. for 24 hours; the methanol was evaporated; the residue was stirred in 6N HCl for 30 minutes, diluted with 30 mL of water and extracted with methylene chloride. The aqueous layer was made basic and extracted with methylene chloride and the extract was dried (Na₂SO₄), filtered and concentrated to 0.065 g of product as a 68/28 ratio of β/α amines.

Step B: Preparation of (2SR,12bRS)-N-(1,3,4,6,7,12b-hexahydro-2H-benzo[b-]furo[2,3-a]quinolizin-2-yl)-2-methylpropane sulfonamide To 0.080 g (0.33 mmol) of the above amine mixture in 3 mL of methylene chloride was added 0.050 g (0.50 mmol) of triethylamine and 0.078 g (0.50 mmol) of isobutylsulfonylchloride. The mixture was stirred 2 hours, poured into 5% NaOH and washed with methylene chloride which was dried (Na₂SO₄), filtered and concentrated to an oil. Chromatography gave the pure (2RS,12bSR)-isomer which after concentration of the rich fractions was taken up in a minimum of ethanol, treated with ethanolic HCl, and ether was added to incipient cloudiness. After crystallization was complete there was collected 0.047 g of product with m.p. 266°–269°C.

Employing the procedure substantially as described in Example 8, but substituting for the quinolizine-2-one, ammonium acetate and sulfonyl chloride used therein, the Ar[2,3-a]quinolizin-2-ones, R³-ammonium acetates and R⁴-sulfonyl chlorides described in Table VI, there are prepared the N-(Ar[2,3-a]quinolizin-2β-yl)amines, also described in Table VI by the following reaction:

TABLE VI

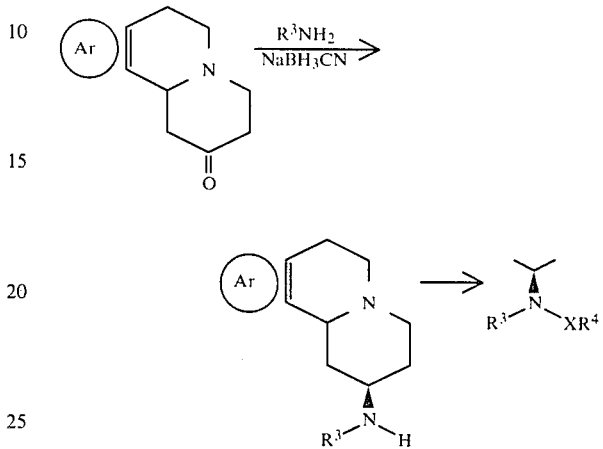

| Ar | R³ | XR⁴ |
|---|---|---|
| benzo[b]furo- | HOCH₂CH₂— | —SO₂CH₂CH(CH₃)₂ |
| benzo[b]furo- | H₂NC(O)—CH₂— | —SO₂(CH₂)₃CH₃ |
| 11-chlorobenzo-[b]furo- | CH₃C(O)NH(CH₂)₂— | —SO₂(CH₂)₂CH₃ |
| 10,11-dimethyl-benzo[b]furo- | HOOCCH₂— | —SO₂CH₂CH₃ |
| benzo[b]thieno- | (CH₃)₂N(CH₂)₂— | —SO₂CH₂CH(CH₃)₂ |

EXAMPLE 9

(2SR,12bRS)-N-Acetyl-N-(1,3,4,6,7,12b-hexahydro-2H-benzo[b]furo[2,3-a]quinolizin-2-yl)-2-methylpropane sulfonamide To a solution of (2SR,12bRS)-N-(1,3,4,6,7,12b-hexahydro-2H-benzo[b]furo[2,3-a]quinolizin-2-yl)-2-methylpropane sulfonamide (362 mg; 1.0 mmol) in 20 mL of dry THF is added NaH (26 mg; 1.1 mmol). After the reaction is stirred 30 minutes at room temperature, a solution of acetyl chloride (86 mg; 1.1 mmol) in 5 mL of dry THF is added dropwise at 0° C. The reaction is warmed to room temperature and evaporated to dryness. The residue is extracted with ethyl acetate to which is then added ethanolic HCl, causing the hydrochloride salt of the product to crystallize.

By substituting for the acetyl chloride used in Example 9, approximately equimolar amounts of methyl formate, butanoyl chloride and heptanoyl chloride, there are produced, respectively the corresponding: (2SR,12bRS)-N-formyl, N-butanoyl and N-heptanoyl-N-(1,3,4,6,7,12b-hexahydro-2H-benzo[b]furo[2,3-a]-quinolizin-2-yl)-2-methylpropane sulfonamide.

EXAMPLE 10

(2SR,12bRS)-N-(1,3,4,6,7,12b-Hexahydro-2H-benzo[b]-furo[2,3-a]quinolizin-2-yl)-1,3-propanesultam

Step A: Preparation of (2SR,12bRS)-N-(1,3,4,6,7,12b-hexahydro-2H-benzo[b]furo[2,3-a]quinolizin-2-yl)-3-chloropropanesulfonamide.HCl To 0.300 g (1.24 mmol) of (2SR,12bRS)- and (2SR,12bSR)-N-(1,3,4,6,7,12b-hexahydro-2H-benzo[b]-furo[2,3-a]quinolizin-2-amine dissolved in 3 ml of methylene chloride and cooled to 0° C. was added 0.150 g (1.49 mmol) of triethylamine and 0.242 g (1.37 mmol) of 3-chlororopanesulfonylchloride. The reaction was stirred 3 hours at 25° C., poured into 5% NaOH and washed with methylene chloride which is dried (Na$_2$SO$_4$), filtered and concentrated. The oil obtained was chromatographed (silica/10% MeOH/CHCl$_3$) giving 0.100 g of pure (2SR,12bSR)-isomer.

Step B: Preparation of (2SR,12 bRS)-N-(1,3,4,6,7,12b-hexahydro-2H-benzo[b]furo[2,3-a]quinolizin-2-yl)-1,3-propanesultam.HCl The above sulfonamide (0.092 g, 0.24 mmol) was dissolved in 3 mL of dimethoxyethane (DME) and 0.055 g (0.48 mmol) of potassium t-butoxide was added. The reactants were heated at 60° C. for 2 hours and then poured into 5% NaOH and extracted with ether. The ether was washed with brine, dried (MgSO$_4$), filtered and concentrated to yield a crude product. Chromatography (silica; 5% MeOH/CHCl$_3$) gave 0.062 g of product. The product was taken up in ethanol, treated with ethanolic HCl and ether to incipient cloudiness. When crystallization was complete the product was collected and dried, m.p. 207°–210° C. (dec).

EXAMPLE 11

(2SR,12bRS)-N-(1,3,4,6,7,12b-Hexahydro-2H-benzo[b]-furo[2,3-a]quinolizin-2-yl)oxazolin-2-one hydro-chloride 0.25 hydrate

Step A: Preparation of (2SR,12bRS)-N-(1,3,4,6,7,12b-Hexahydro-2H-benzo[b]furo[2,3-a]quinolizin-2-yl)-N-(2-hydroxyethyl)amine Ethanolamine (0.366 g, 6 mmol) and 0.241 g (1 mmol) of (2SR,12bRS)-1,3,4,6,7,12b-hexahydro-2H-benzo[b]furo[2,3-a]quinolizin-2-one were dissolved in 20 mL dry methanol, and ethanolic HCl added until the pH was 6.5. To this was added 0.038 g (0.6 mmol) of sodium cyanoborohydride and 3A molecular sieves. After stirring 18 hours, NH3 saturated CHCl$_3$ was added until basic, and the solvent removed in vacuo. The residue was stirred in ethyl acetate, filtered and the solvent removed in vacuo. Purification by spinning disc chromatography (silica; NH3 saturated CHCl$_3$) afforded 0.063 g (36%) of o-isomer and 0.112 g (64%) of β-isomer in 61% overall yield. The desired β-isomer was recrystallized from ether/pet. ether to yield white needles with m.p. 131°–132° C.

Step B: Preparation of (2SR,12bRS)-N-(1,3,4,6,7,12b-hexahydro-2H-benzo[b]furo[2,3-a]quinolizin-2-yl)-oxazolin-2-one hydrochloride 0.25 hydrate (2SR,12bRS)-N-(1,3,4,6,7,12b-Hexahydro-2H-benzo[b]furo-[2,3-a]-quinolizin-2-yl)-N-(2-hydroxyethyl)amine (0.71 g, .25 mmol) was placed in 5 ml dry toluene, and enough THF was added to make it homogeneous. To this was added dropwise 0.205 g (1.25 mmol) of carbonyl diimidazole in 2 ml dry toluene, and the reaction was refluxed 18 hours, after which time it was cooled and the solvent evaporated. Purification by spinning disc chromatography (silica; 5% (v/v) MeOH/CHCl$_3$) gave 0.062 g (0.2 mmol) of (2SR,12bRS)-N-(1,3,4,6,7,12b-hexahydro-2H-benzo[b]furo[2,3-a]quinolizin-2-yl)oxazolin-2-one in 79% yield. This was dissolved in ethyl acetate and ethanolic HCl was added dropwise to yield the hydrochloride 0.25 hydrate salt as a yellow solid, with m.p. 230° C. (dec).

EXAMPLE 12

(2SR,12bRS)-N-(1,3,4,6,7,12b-Hexahydro-2H-benzo[b]-furo[2,3-a]quinolizin-2-yl)succinimide A mixture of (2SR,12bRS)-(1,3,4,6,7,12b-Hexahydro-2H-benzo[b]furo[2,3-a]quinolizin-2-yl)amine (80 mg; 0.33 mmol) and succinic anhydride (33 mg; 0.33 mmol) is heated under nitrogen at 130° C. for 2 hours. The residue is extracted into ethyl acetate which is washed with saturated NaHCO$_3$ solution. The organic phase is dried (Na$_2$SO$_4$), filtered and acidified with ethanolic HCl, causing the hydrochloride salt of the product to crystallize.

Employing maleic anhydride and glutaric anhydride in place of the succinic anhydride in Example 11, affords; respectively (2SR,12bRS)-N-(1,3,4,6,7,12b-hexahydro-2H-benzo[b]-furo[2,3-a]-quinolizin-2-yl)maleimide; and
(2SR,12bRS)-N-(1,3,4,6,7,12b-hexahydro-2H-benzo[b]-furo[2,3-a]quinolizin-2-yl)glutarimide.

EXAMPLE 13

(2SR,10bRS)-N-(1,3,4,6,7,10b-Hexahydro-2H-thiazolo[4,5-a]quinolizin-2-yl)-N,N',N'-trimethylsulfamide, hydrochloride

Step A: Preparation of Ethyl 4-oxo-pipecolinate, ethylene ketal

A solution of ethyl 4-oxo-pipecolinate (17.1 g; 0.1 mole), ethylene glycol (6.8 g; 0.11 mole), and p-toluenesulfonic acid (0.5 g) in 250 mL of dry benzene is refluxed under Dean-Stark conditions for 18 hours. The benzene solution is washed with saturated aqueous NaHCO$_3$ solution, dried (Na$_2$SO$_4$), and evaporated to afford the desired product.

Step B: Preparation of Ethyl N-(3-Ethoxycarbonylpropyl)-4-oxopipecolinate, ethylene ketal A mixture of ethyl 4-oxopipecolinate, ethylene ketal (12.9 g; 60 mmol), ethyl 4-bromobutyrate (12.9 g; 66 mmol), and K$_2$CO$_3$ (12.0 g; 86 mmol) in 250 mL of toluene is heated at 80° C. for 4 hours. The solid is then filtered off, and the filtrate is concentrated. Distillation of the residue affords the product.

Step C: Preparation of 1,3,4,6,7,8,9,9a-Octahydro-2H-quinolizin-1,8-dione-2-carboxylic acid, ethyl ester, 8-ethylene ketal Ethyl N-(3-ethoxycarbonylpropyl)-4-oxopipecolinate, ethylene ketal (3.29 g; 10 mmol) is added to a stirred suspension of NaH (0.58 g of a 50% dispersion in oil; 12 mmol) in 5mL of dry toluene. The reaction is then refluxed for 2 hours. Water is added, followed by acetic acid until the reaction is neutral. The oganic fraction is separated, dried (Na$_2$SO$_4$), and concentrated to yield the crude product.

Step D: Preparation of
1,3,4,6,7,8,9,9a-Octahydro-2H-quinolizin-1,8-dione, 8-ethylene ketal A mixture of 1,3,4,6,7,8,9,9a-octahydro-2H-quinolizin-1,8-dione-2-carboxylic acid, ethyl ester, 8-ethylene ketal (2.83 g; 10 mmol), LiCl (0.84 g; 20 mmol), and water (0.36 g; 20 mmol) in 25 mL of DMSO is heated to 180° C. for 2 hours. After the reaction is cooled to room temperature, it is partitioned between ethyl acetate and water. The organic extracts are separated, dried (Na$_2$SO$_4$), and concentrated. The residue is chromatographed over silica gel to give the product.

Step E: Preparation of
2-Bromo-1,3,4,6,7,8,9,9a-Octahydro-2H-quinolizin-1,8-dione, 8-ethylene ketal To a solution of 1,3,4,6,7,8,9,9a-octahydro-2H-quinolizin-1,8-dione, 8-ethylene ketal (2.1 g; 10 mmol) in 20 mL of dry methylene chloride is added dropwise a solution of benzyltrimethylammonium bromide perbromide (3.9 g; 10 mmol) in 10 mL of methylene chloride at 0° C. After 2 hours, the reaction mixture is washed three time with water. The orgainic phase is dried (Na ) and concentrated in vacuo to yield the crude product which is used without further purification.

Step F: Preparation of
1,3,4,6,7,10b-Hexahydro-2H-thiazolo[4,5-a]quinolizin-2-one, ethylene ketal A solution of 2-bromo-1,3,4,6,7,8,9,9a-octahydro-2H-quinolizin-1,8-dione, 8-ethylene ketal (4.3 g; 15 mmol) and thioformamide (1,8 g; 30 mmol) in 10 mL of DMF is stirred with 2.0 g of 3A-molecular sieves at 50° C. for 8 hours. After the solid is filtered, the filtrate is poured into water, causing the product to crystallize.

Step G: Preparation of
1,3,4,6,7,10b-Hexahydro-2H-thiazolo[4,5-a]quinolizin-2-one 1,3,4,6,7,10b-Hexahydro-2H-thiazolo[4,5-a]-quinolizin-2-one, ethylene ketal (1.0 g) is dissolved in 25 mL of acetone. 6N HCl (2.0 mL) is added, and the reaction is stirred at room temperature for 4 hours. The acetone is removed in vacuo, and the aqueous fraction is made basic with K$_2$CO$_3$. This methylene chloride (3×10 mL). The organic extracts are then dried (Na$_2$SO$_4$) and concentrated to afford the product.

Following the procedures substantially as described in Example 1, Steps F and G but substituting for the quinolizin-2-one used therein, an equimolar amount of the quinolizin-2-one from Step G of this Example 12, there are produced in sequence:
(2RS,10bSR)-N-(1,3,4,6,7,10b-hexahydro-2H-thiazolo-[4,5-a]quinolizin-2-yl)-N-methylamine; and
(2RS,10bSR)-N-(1,3,4,6,7,10b-hexahydro-2H-thiazolo-[4,5-a]quinolizin-2-yl)-N,N',N'-trimethylsulfamide, hydrochloride.

Similarly prepared are those compounds wherein Ar is thiazolo and —X—R$^4$ are —SO$_2$CH$_2$OH$_2$$_0$H, —SO$_2$CH$_2$CH$_3$, and —SO$_2$(CH$_2$)$_3$OH.

EXAMPLE 14

(2SR,10bRS)-N-(1,3,4,6,7,10b-Hexahydro-2H-imidazolo-[4,5-a]quinolizin-2-yl)-N,N',N'-trimethylsulfamide, hydrochloride Step A: Preparation of
(10bRS)-1,3,4,6,7,10b-hexa-hydro-2H-imidazo[4,5-a]quinolizin-2-one, ethylene ketal Formamidine acetate (3.1 g; 30 mmol) is added to a solution of 2-bromo-1,3,4,6,7,8,9,9a-octahydro-2H-quinolizin-1,8-dione, 8-ethylene ketal (4.3 g; 15 mmol) in 15 mL of ethanol. The reaction is refluxed for 3 hours and then concentrated. The residue is partitioned between ethyl acetate and saturated NaHCO$_3$. The organic fraction is dried (Na$_2$SO$_4$) and evaporated to yield the desired product, after chromatography over silica gel.

Step B: Preparation of
(10bRS)-1,3,4,6,7,10b-Hexahydro-2H-imidazo[4,5-a]quinolizin-2-one.

(10bRS)-1,3,4,6,7,10b-Hexahydro-2H-imidazo-[4,5-a]quinolizin-2-one, ethylene ketal (2.0 g) is dissolved in 25 mL of a mixture of acetone-6N HCl (10:1) and stirred at room temperature for 6 hours. The acetone is removed in vacuo, and the aqueous fraction is made basic with K$_2$CO$_3$. This mixture is extracted with methylene chloride. The organic extracts are then dried (Na$_2$SO$_4$) and concentrated to afford the product.

Following the procedures substantially as described in Example 1, Steps F and G but substituting for the quinolizin-2-one used therein, an equimolar amount of the quinolizin-2-one from Step B of this Example 14 there are produced in sequence:
(2SR,10bRS)-N-(1,3,4,6,7,10b-hexahydro-2H-imidazolo-[4,5-a]quinolizin-2-yl)-N-methylamine; and
(2SR,10bRS)-N-(1,3,4,6,7,10b-hexahydro-2H-imidazolo-[4,5-a]quinolizin-2-yl)-N,N',N'-trimethylsulfamide, hydrochloride.

Similarly prepared are those compounds wherein Ar is imidazo and —X—R$^4$ are —SO$_2$(CH$_2$)$_2$OH—, SO$_2$(CH$_2$)$_3$OH, and SO$_2$CH$_2$CH$_3$.

EXAMPLE 15

(2SR,10bRS)-N-(1,3,4,6,7,10b-Hexahydro-2H-pyrazolo-[3,4-a]quinolizin-2-yl)-N,N',N'-trimethylsulfamide, hydrochloride Step A: Preparation of
(10SR)-1,3,4,6,7,10-Hexahydro-2H-pyrazolo[3,4-a]quinolizin-2-one, ethylene ketal (9aSR)-1,3,4,6,7,8,9,9a-Octahydro-2H-quinolizin-1,8-dione, 8-ethylene ketal (4.2 g; 20 mmol) and DMF-dimethyl acetal (2.86 g; 24 mmol) are heated at 100° C. under nitrogen for 16 hours. The dark residue is then dissolved in 5 mL of ethanol and treated with anhydrous hydrazine (1.28 g; 40 mmol). The reaction is stirred at room temperature for 18 hours. The solvent is evaporated, and the residue is chromatographed over silica gel, eluting with 5% MeOH/ CHCl$_3$ saturated with ammonia to yield the product.

Step B: Preparation of (10SR)-1,2,3,4,6,7,10-Hexahydro-2H-pyrazolo[3,4-a]quinolizin-2-one 1,2,3,4,6,7,10-Hexahydro-2H-pyrazolo[3,4-a]-quinolizin-2-one, ethylene ketal (1.0 g) is dissolved in 25 mL of a mixture of acetone-6N HCl (10:1) and stirred at room temperature for 5 hours. The acetone is removed in vacuo, and the aqueous fraction is made basic with $K_2CO_3$. This mixture is extracted with methylene chloride. The organic extracts are then dried ($Na_2SO_4$) and concentrated to afford the product.

Following the procedure substantially as described in Example 1, Steps F and G but substituting for the quinolizin-2-one used therein, an equimolecular amount of the quinolizin-2-one from Step B of this Example 15, there are produced in sequence.
(2SR,10bRS)-N-(1,3,4,6,7,10b-hexahydro-2H-pyrazolo-[3,4-a]quinolizin-2-yl)-N-methylamine; and
(2SR,10bRS)-N-(1,3,4,6,7,10b-hexahydro-2H-pyrazolo-[3,4-a]quinolizin-2-yl)-N,N',N'-trimethylsulfonamide.

Similarly prepared are those compounds wherein Ar is pyrazolo and $-XR^4$ are $-SO_2(CH_2)_2OH$, $-SO_2(CH_2)_3OH$ and $-SO_2CH_2CH_3$.

EXAMPLE 16

(2SR,11bRS)-N-(1,3,4,6,7,11b-Hexahydro-2H-pyrido-[2,3-a]quinolizin-2-yl)-N,N',N'-trimethylsulfamide, hydrochloride

Step A: Preparation of 2-(2-(1,3-Dioxolan-2-yl)ethyl)-1,3,4,6,7,8,9,9a-Octahydro-2H-quinolizin-1,8-dione-2-carboxylic acid, ethyl ester, 8-ethylene ketal 1,3,4,6,7,8,9,9a-Octahydro-2H-quinolizin-1,8-dione-2-carboxylic acid, ethyl ester, 8-ethylene ketal (5.7 g; 20 mmol) is added in small portions to a stirred suspension of NaH (0.48 g; 20 mmol) in 50 mL of toluene/DMF (1:1). After 15 minutes 2-(2-bromoethyl)-1,3-dioxolane is added in one portion, and the reaction is refluxed for 4 hours. The mixture is cooled and partitioned between water and ethyl acetate. The organic layer is washed well with water, dried ($Na_2SO_4$), and concentrated. The residue is chromatographed over silica gel to afford the product.

Step B: Preparation of 2-(2-(1,3-Dioxolan-2-yl)ethyl)-1,3,4,6,7,8,9,9-aoctahydro-2H-quinolizin-1,8-dione, 8-ethylene ketal A mixture of 2-(2-(1,3-dioxolan-2-yl)ethyl)-1,3,4,6,7,8,9,9a-octahydro-2H-quinolizin-1,8-dione-2-carboxylic acid, ethyl ester, 8-ethylene ketal (1.9 g; 5 mmol), LiCl (0.42 g; 10 mmol), water (0.18 g; 10 mmol), and 20 mL DMSO is heated at 180° C. for 2 hours. The reaction is then poured into 100 mL of water and extracted with ethyl acetate. The organic fraction is washed well with water, dried ($Na_2SO_4$), and concentrated. The residue is chromatographed over silica gel to yield the desired product.

Step C: Preparation of (2SR,11bRS)-1,3,4,6,7,11b-Hexahydro-2H-pyrido[2,3-a]quinolizin-2-one, ethylene ketal A Solution of 2-(2-(1,3-dioxolan-2-yl)ethyl)-1,3,4,6,7,8,9,9a-octahydro-2H-quinolizin-1,8-dione, 8-ethylene ketal (1.5 g; 5 mmol) and hydroxylamine hydrochloride (0.7 g; 10 mmol) in 25 mL absolute ethanol is refluxed for 2 hours. The solvent is evaporated, and the residue is chromatographed over silica gel to give the product.

Step D: Preparation of (2SR,11bRS)-1,3,4,6,7,11b-Hexahydro-2H-pyrido[2,3-a]quinolizin-2-one A Solution of 1,3,4,6,7,11b-hexahydro-2H-pyrido[2,3-a]quinolizin-2-one, ethylene ketal (2.0 g) in 50 mL of acetone/6N HCl (10:1) is stirred at room temperature for 3 hours. The acetone is removed in vacuo, and the aqueous fraction is made basic with $K_2CO_3$. The resulting mixture is extracted with methylene chloride, which is then dried ($Na_2SO_4$) and concentrated to afford the product.

Employing the procedures substantially as described in Example 1, Steps F and G but substituting for the quinolizin-2-one used therein, an equimolar amount of the quinolizin-2-one from Step D of this Example 16, there are produced in sequence:
(2SR,11bRS)-N-(1,3,4,6,7,11b-hexahydro-2H-pyrido-[2,3-a]quinolizin-2-yl)-N-methylamine; and
(2SR,11bRS)-N-(1,3,4,6,7,11b-hexahydro-2H-pyrido-[2,3-a]quinolizin-2-yl)-N,N',N'-trimethylsulfamide, hydrochloride.

Similarly prepared are those compounds wherein Ar is pyrido and $XR_4$ is $-SO_2(CH_2)_2OH$, $SO_2(CH_2)_3OH$ and $SO_2CH_2CH_2$.

Pharmaceutical Formulations

EXAMPLE 17

| Ingredient | Mg/Capsule |
| --- | --- |
| (2SR,12bRS)—N—(1,3,4,6,7,12b-Hexahydro-2H—benzo[b]furo[2,3-a]-quinolizin-2-yl)-N,N',N'—trimethylsulfamide.HCl | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 18

| Ingredient | Mg/Capsule |
| --- | --- |
| (2SR,12bRS)—N—(1,3,4,6,7,12b-Hexahydro-2H—benzo[b]furo[2,3-a]-quinolizin-2-yl)-N—methyl-2-hydroxyethanesulfonamide.HCl | 6 |
| starch | 87 |
| magnesium stearate | 7 |

EXAMPLE 19

Effect of $\alpha_2$-adrenoceptor antagonists upon colonic muscle activity in anesthetized cats Cats were anesthetized with vinbarbital (50 mg/kg i.v.) and allowed to stabilize following the placement of strain gauges to measure longitudinal and circular muscle activity in the descending colon. Bethanechol was then infused over 60 minutes at a rate of 3 μg/kg/min., and after 30 minutes, drug or vehicle was infused over 5 minutes.

The results are shown in the following table:

| Compound | Dose (i.v.) | N | Reduction in Circular Muscle Contractility |
|---|---|---|---|
| L-646,488-001U | 1,000 μg/kg | 4 | 4/4 |
| L-654,979-001J | 250 μg/kg | 4 | 4/4 |
| L-654,284-001P | 300 μg/kg | 4 | 4/4 |

No consistent effects of these compounds were found upon longitudinal smooth muscle contractility.

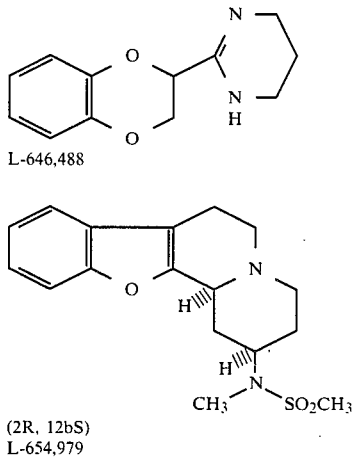

L-646,488

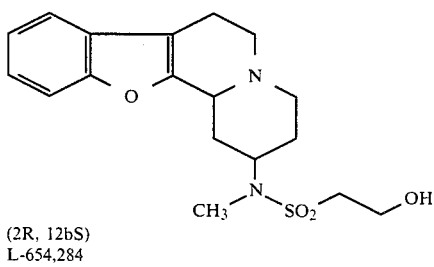

(2R, 12bS)
L-654,979

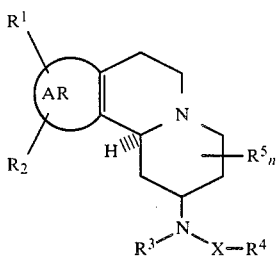

(2R, 12bS)
L-654,284

What is claimed is:

1. A method of treating colonic spasm, irritable bowel syndrome and constipation which comprises adminstering to a patient in need of such treatment an effective amount of a selective $\alpha_2$-adrenergic receptor antagonist of structural formula:

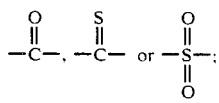

or a pharmaceutically acceptable salt thereof wherein Ar represents an aromatic heterocycle selected from $R^1,R^2$-benzo[b]furo-, or $R^1,R^2$-benzo[b]thieno-, $R^1$ and $R^2$ are independently:
(1) hydrogen,
(2) halo,
(3) hydroxy,
(4) $C_{1-3}$alkoxy, or
(5) $C_{1-6}$alkyl;

$R^3$ is
(1) hydrogen,
(2)

wherein R is hydrogen or $C_{1-3}$alkyl,
(3) $C_{1-6}$alkyl, either unsubstituted or substituted with one or more of;
 (a) hydroxy,
 (b) carboxy,
 (c) $C_{1-3}$alkoxycarbonyl,
 (d) halo,
 (e) $C_{1-3}$alkoxy,
 (f) —CONR$^6$R$^7$, wherein R$^6$ and R$^7$ are the same or different and are hydrogen or $C_{1-5}$alkyl, or joined together directly to form a 5–7 membered ring or through a heteroatom selected from O, N and S, to form a 6-membered heterocycle with the nitrogen to which they are attached, or
 (g) —NR$^6$R$^7$;

X is $$-\overset{O}{\underset{\|}{C}}-, -\overset{S}{\underset{\|}{C}}- \text{ or } -\overset{O}{\underset{\underset{O}{\|}}{\overset{\|}{S}}}-;$$

and
R4 is
(1) —OR$^8$, wherein R$^8$ is hydrogen or $C_{1-6}$ alkyl, either unsubstituted or substituted with one or more of;
 (a) OR, or
 (b) —NRCOR;
(2) —N(R$^8$)$_2$,
(3) —CO$_2$R$^8$,
(4) —CONR$^6$R$^7$,
(5) $C_{1-6}$ alkyl, either unsubstituted or substituted with
 (a) OR$^8$,
 (b) halo,
 (c) CO$_2$R$^8$,
 (d) CONR$^6$R$^7$,
(6) $C_{2-5}$alkenyl,
(7) $C_{2-5}$alkynyl,
(8) $C_{3-6}$cycloalkyl,
(9) 5 or 6-membered heterocycle with up to 2 heteroatoms selected from N, O, and S,
(10) carbocyclic aryl of 6-10 carbon atoms, either unsubstituted or substituted with one or more of;
 (a) halo, or
 (b) OR; or R$^5$ is independently
(1) $C_{1-6}$ alkyl, either unsubstituted or substituted with one or more of
 (a) —OR$^8$,
 (b) —NR$^8$COR$^8$, or
 (c) —CO$_2$R$^8$,
(2) —CO$_2$R$^8$, or
(3) —CONR$^6$R$^7$;
n is 0, 1, 2 or 3; and
R$^3$ and R$^4$ taken together directly or through a heteroatom selected from O, N and S, to form a 5- or 6-membered heterocycle with the nitrogen to which they are attached; or $R^3$ and $R^5$ or $R^4$ and $R^5$, if $R^5$ is in the 1- or 3-position and both are alkyl, can be joined together to form a 5- or 6-membered ring.

2. The method of claim 1 wherein Ar is $R^1$, $R^2$-benzo[b]furo- or $R^1$,$R^2$-benzo[b]thieno—; $R^1$ and $R^2$ are hydrogen or halo; $R^3$ is $C_{1-6}$alkyl, X is —$SO_2$—and $R^4$ is $C_{1-6}$alkyl, di ($C_{1-3}$alkyl)-amino, halo-$C_{1-6}$alkyl, hydroxy-$C_{1-6}$alkyl, $C_{2-5}$alkenyl, $C_6$-$_{10}$carbocyclic aryl, 5 or 6-membered heterocycle, —$CO_2R^8$, —$C_{1-5}$alkyl—$CO_2R^8$ or —$C_{1-6}$alkyl—$CONR^6R^7$; and $R^5$ is hydrogen or $C_{1-6}$alkyl.

3. The method of claim 2 wherein $R^1$ and $R^2$ are hydrogen, $R^3$ is methyl, $R^4$ is C hydroxy-C, di($C_{1-3}$alkyl)amino, 2-furfuryl, or $C_{1-3}$alkoxycarbonylethyl and R5 is hydrogen.

4. The method of claim 3, wherein Ar is benzo[b]furo-, $R^3$ is $CH_3$, X is —$SO_2$—, and $R^4$ is —$CH_2CH_3$, —$N(CH_3)_2$, —$CH_2CH_2OR$ or —$CH_2CH_2CH_2OR$ wherein $R^5$ is hydrogen or methyl.

5. The method of claim 4 wherein the compound is:
(a) (2R,12bS)-N-(1,3,4,6,7,12b-hexahydro-2H-benzo[b]furo[2,3-a]quinolizin-2-yl)-N-methyl-2-hydroxyethanesulfonamide;
(b) (2RS,12bSR)-N-(1,3,4,6,7,12b-hexahydro-2H-benzo-[b]furo[2,3-a]quinolizin-2-yl)-N-methyl-3-hydroxypropanesulfonamide;
(c) (2R,12bS)-N-(1,3,4,6,7,12b-hexahydro-2H-benzo[b]furo[2,3-a]quinolizin-2-yl)-N-methyl-methanesulfonamide;
(d) (2R,12bS)-N-(1,3,4,6,7,12b-hexahydro-2H-benzo-[b]-furo[2,3-a]quinolizin-2-yl)-N,N',N'-trimethylsulfamide; or
(e) (2RS,12bSR)-N-(1,3,4,6,7,12b-hexahydro-2H-benzo-[b]thieno[2,3-a]quinolizin-2-yl)-N-methyl-methanesulfonamide;

or a pharmaceutically acceptable salt thereof.

* * * * *